(12) United States Patent
Martin

(10) Patent No.: US 7,435,228 B2
(45) Date of Patent: Oct. 14, 2008

(54) HIGH FIDELITY HEARING RESTORATION

(75) Inventor: G. Patrick Martin, Merrit Island, FL (US)

(73) Assignee: Harris Corporation, Melbourne, FL (US)

( * ) Notice: Subject to any disclaimer, the term of this patent is extended or adjusted under 35 U.S.C. 154(b) by 776 days.

(21) Appl. No.: 10/622,748

(22) Filed: Jul. 18, 2003

(65) Prior Publication Data

US 2005/0013445 A1    Jan. 20, 2005

(51) Int. Cl.
  A61B 5/00    (2006.01)
  A61B 5/12    (2006.01)
  H04R 29/00   (2006.01)
  H04R 25/00   (2006.01)
  H04R 3/02    (2006.01)
  A61N 1/00    (2006.01)

(52) U.S. Cl. .......... 600/559; 381/60; 381/317; 381/73.1; 73/585; 607/55; 607/57

(58) Field of Classification Search .......... 381/60, 381/317, 73.1; 607/55, 57; 600/559, 25; 73/585

See application file for complete search history.

(56) References Cited

U.S. PATENT DOCUMENTS

| | | | |
|---|---|---|---|
| 4,680,798 A * | 7/1987 | Neumann ............ 381/320 |
| 5,403,262 A | 4/1995 | Gooch | |
| 6,047,074 A | 4/2000 | Zoels et al. | |
| 6,080,112 A | 6/2000 | Don | |
| 6,155,971 A | 12/2000 | Calhoun et al. | |
| 6,210,321 B1 | 4/2001 | Di Mino et al. | |
| 6,394,947 B1 | 5/2002 | Leysieffer | |
| 6,602,202 B2 * | 8/2003 | John et al. ............ 600/559 |
| 6,682,472 B1 * | 1/2004 | Davis ................ 600/25 |
| 2002/0146137 A1 | 10/2002 | Kuhnel et al. | |
| 2004/0141624 A1 * | 7/2004 | Davis et al. .......... 381/73.1 |

* cited by examiner

*Primary Examiner*—Vivian Chin
*Assistant Examiner*—Devona E. Faulk
(74) *Attorney, Agent, or Firm*—Darby & Darby PC; Robert J. Sacco

(57) ABSTRACT

Method for accurately measuring hearing loss includes the steps of selecting a series of audio tones within the normal range of hearing (502) and then measuring a relative sensitivity of a test subject with respect to the ability to hear each of the audio tones, exclusive of the effects of tinnitus. (504, 506, 508, 510, 512) The relative sensitivity of the test subject to hear the tones can be measured by determining (510) for each tone an intensity necessary for the test subject to hear the tones at a subjectively equal loudness level which is selected to exceed a perceived level of noise attributable to tinnitus for the test subject.

10 Claims, 7 Drawing Sheets

HIGH FIDELITY HEARING RESTORATION

BACKGROUND OF THE INVENTION

1. Statement of the Technical Field

The inventive arrangements relate generally to hearing aids, and more particularly to methods and apparatus for achieving high fidelity hearing restoration.

2. Description of the Related Art

Human hearing generally has a frequency range of between about 20 to 20 kHz. It is well known among hearing experts that among those people experiencing hearing loss, the ability to hear will generally vary over this range of audio frequencies. Consequently, a loss of hearing has a more profound effect than merely decreasing the overall volume or perceived sound level. In fact, because hearing loss can be more significant within certain frequency ranges as compared to other frequency ranges, the diminished hearing commonly creates difficulties in allowing hearing impaired individuals to understand words which are spoken to them.

One reason for this difficulty in understanding spoken words is that loss of hearing often first begins to occur at the higher frequencies within the audible range. Since many common sounds in spoken English include these high frequency components, people with diminished hearing can often hear these spoken words only in a garbled way because key audio information is being lost in the communication channel.

The conventional solution to addressing the foregoing problem is to provide additional audio gain at those frequencies where there has been a measured loss of hearing. The most common way of providing such gain is through the use of hearing aids. Although there are several different types of hearing aids available, the basic goal of such devices is essentially the same. They amplify selected ranges of audio frequencies and provide the amplified acoustic energy to the eardrum, especially at those frequencies where there has been a measured loss of hearing. Most current digital hearing aid processors have Nyquist sampling rates that will support audio frequencies up to about 10 kHz. However, typical output transducers in such devices will generally only support audio frequencies up to about 6 kHz. Similarly, most analog hearing aids also address frequencies up to about 6 KHz, a range typically associated with "telephone" quality acoustics. However, many current approaches to high fidelity hearing restoration correctly address frequencies above 10 KHz.

The conventional method for evaluating the degree of hearing loss, and the amount of audio gain required at various frequencies, is typically determined based on threshold of hearing (TOH) testing. The TOH is lowest level sound that can be perceived by the human auditory system at a particular frequency. Thus, the testing usually involves a series of tones at various measurement points within the audible frequency range. When plotted, the data for an individual with normal hearing will generally fall on a predictable curve or contour that was first demonstrated by Fletcher and Munson at Bell Labs in the 1930s. The curves are lowest in the range from 1 to 5 kHz, with a dip between 3 and 4 kHz, indicating that individuals are generally most sensitive to frequencies in this range. The intensity of audio tones above or below this range must be raised substantially in order to create the same impression of loudness to an individual.

By comparing an individual's measured TOH to normal TOH values it is possible to make certain conclusions regarding the degree of hearing loss at each frequency. The conventional approach is to then use this information as a basis for setting the gain characteristics of a hearing aid device in an effort to increase the level of those audio frequency ranges so as to compensate for the measured degradation in hearing.

Still, many people find that hearing aids produce only marginally improved intelligibility. For example, some studies have shown that persons fitted with hearing aids only achieve 5% to 15% improvements in intelligibility. Users also tend to complain that the hearing they experience is loud and tinny. These poor results have been puzzling and continue despite many apparent improvements in hearing aid technology.

Tinnitus is another condition that affects the hearing of many individuals. Tinnitus is the perception of ringing, hissing, or other sounds in the ears or head when no external sound is present. For many, advancing age is accompanied by a certain amount of hearing impairment combined with symptoms of tinnitus. This can be explained to some extent by recent discoveries suggest that the onset of tinnitus may be linked to natural feedback mechanisms operating improperly when hearing loss occurs. Tinnitus noise is often about 50 dB over TOH and typically has frequencies above 1 kHz. Unfortunately, there is no specific treatment for tinnitus that has proven to be particularly effective.

SUMMARY OF THE INVENTION

The invention concerns a method for accurately measuring hearing loss. The method includes the steps of selecting a series of audio tones within the normal range of hearing and then measuring a relative sensitivity of a test subject with respect to the ability to hear each of the audio tones, exclusive of the effects of tinnitus. The relative sensitivity of the test subject to hear the tones can be measured by determining for each tone an intensity necessary for the test subject to hear the tones at a subjectively equal loudness level. The intensity of the subjectively equal loudness level can advantageously be selected to exceed a perceived level of noise attributable to tinnitus for the test subject. The method can also include the step of determining a difference between the measured intensity and an intensity predicted by a standard loudness contour. For example, the standard loudness contour can be a Fletcher-Munson Loudness Contour. Finally, the method can also include measuring a noise level attributable to tinnitus.

According to another aspect, the invention can include a method for setting a frequency dependent audio gain of a hearing aid device for a person suffering from tinnitus. In that case, the method can include the steps of measuring a test subject's loss of hearing attributable exclusively to dispersion in the hearing channel, and setting for each of a plurality of frequency bands of the hearing aid device an audio gain level to compensate exclusively for the dispersion loss. The measuring step can be performed essentially as described above or by any other suitable means.

According to yet another aspect, the invention can include a method for providing high fidelity hearing restoration. The method can include measuring a test subject's loss of hearing attributable exclusively to dispersion in the hearing channel and fitting the test subject with a hearing aid device in which each of a plurality of frequency bands of the hearing aid device have an audio gain level set to compensate exclusively for the dispersion loss.

Finally, the invention can comprise a hearing aid device for a person suffering from tinnitus. The hearing aid device can include an audio amplification device having a plurality of audio frequency bands with selectable gain levels. Further, each of the gain levels can be set for producing a predetermined amount of audio gain to compensate exclusively for dispersion losses in the hearing channel.

DETAILED DESCRIPTION OF THE PREFERRED EMBODIMENTS

Figure 1:
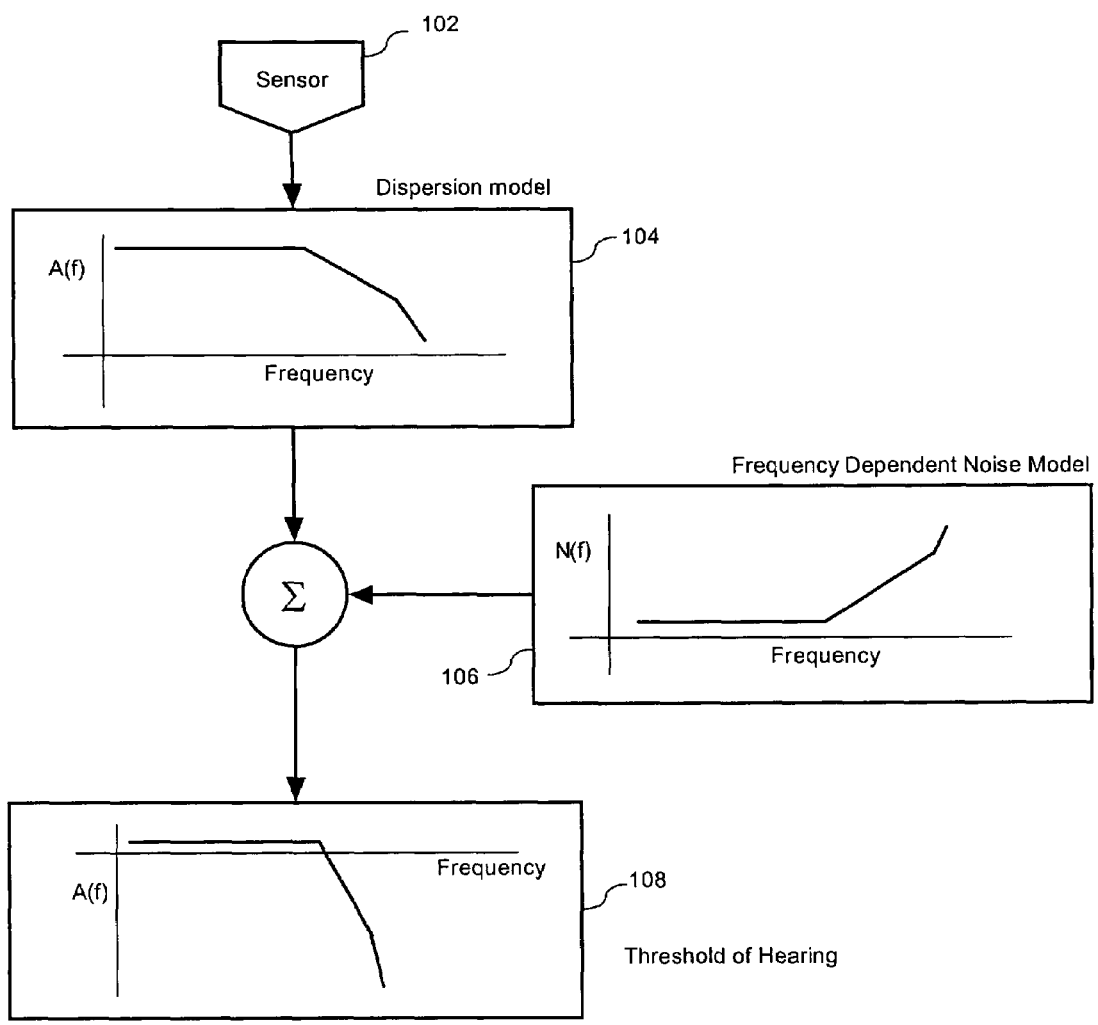
FIG. 1 is a block diagram illustration that is useful for understanding the effects of dispersion losses and noise in the hearing channel.

In order to understand the problem with conventional hearing restoration techniques, it is useful to consider the human ear as a simple communication channel. Referring to FIG. 1, the hearing channel can be conceptually modeled as including audio sensor 102 with an undistorted frequency response within the audio frequency band. As shown in FIG. 1, the output of the sensor 102 can be modified in accordance with a transfer function of a dispersion model 104. As used herein, dispersion refers to hearing losses that reflect a true loss of hearing sensitivity as opposed to losses attributable to the effects of tinnitus noise in the channel. The dispersion model 104 is a simple linear representation of the hearing attenuation that commonly occurs for many persons, especially older persons, suffering from hearing loss. It may be noted that the dispersion model 104 rolls off somewhat at higher frequencies, reflecting greater attenuation (and lessened ability to hear) received audio at those frequencies. This is a true loss of hearing sensitivity at the higher frequencies.

For persons who only suffer from a loss of hearing, the hearing channel can be modeled completely as described above. However, for many others who experience tinnitus, the model is somewhat more complicated. Tinnitus is the perception of ringing, hissing, or other sounds in the ears or head when no external sound is present. In order to take these effects into account, a frequency dependent noise model 106 is introduced in FIG. 1. The frequency dependent noise model represents noise which is added to the audio information in the communication channel as a result of a tinnitus condition.

Figure 4:
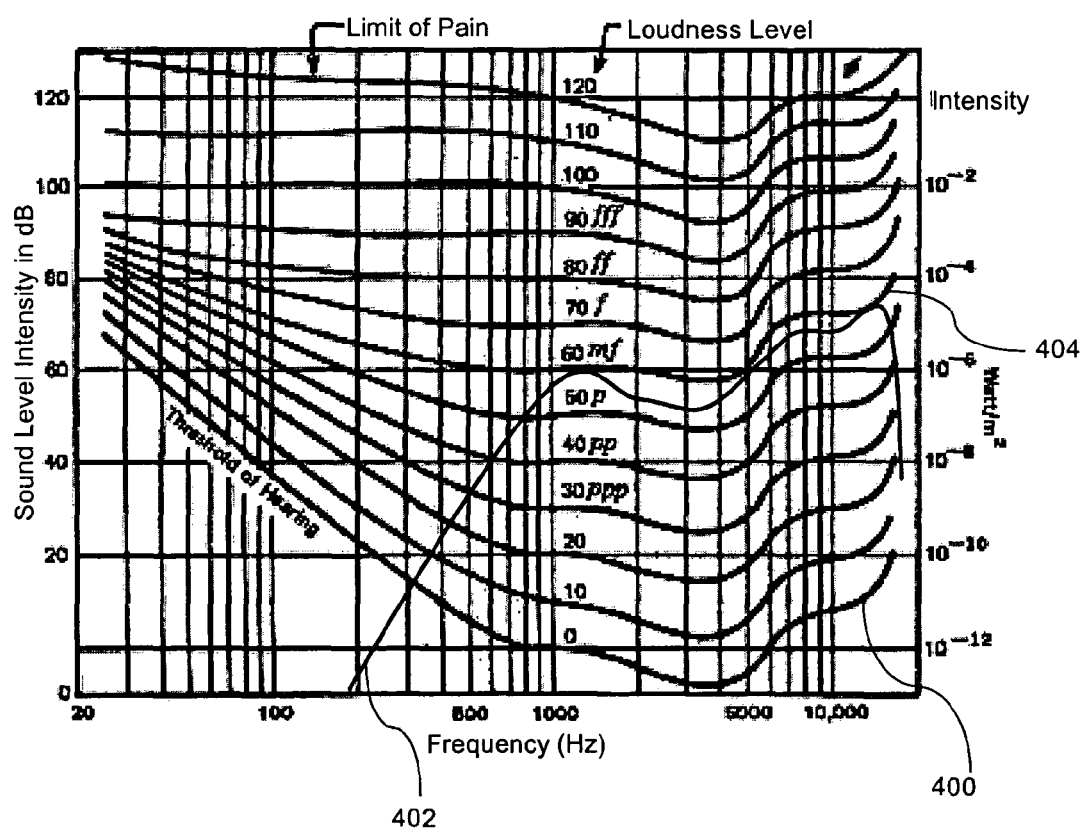
FIG. 4 is a series of Fletcher-Munson curves that are useful for understanding the invention.

When a threshold of hearing (TOH) test is performed, a series of tones are generated to determine the lowest level sound that can be perceived by the human auditory system at a particular frequency. When plotted, the data for an individual with normal hearing will generally fall on a standard curve or contour called a Fletcher-Munson curve. However, when the effects of the dispersion model 104 and the frequency dependent noise model 106 are introduced, the curve will look quite different. A set of Fletcher-Munson curves are shown in FIG. 4. The curve 400 in FIG. 4 is the TOH curve.

As would be expected, the effects of loss of hearing (dispersion model 104) will result in a decreased sensitivity at higher frequencies. However, there is another important consideration that has a profound effect on the TOH test. Because tinnitus noise can be about 50 dB over TOH levels, it will seriously reduce the usable sensitivity at frequencies where tinnitus noise is prevalent (usually above 1 kHz). Simply put, the tinnitus noise masks high frequency sounds that could otherwise be perceived. The effect is illustrated in FIG. 4 where curve 402 is superimposed on the set of Fletcher-Munson. Curve 402 shows an example of perceived noise levels attributable to tinnitus. Audio tones beneath the curve 402 will be substantially masked by the tinnitus.

The effect is also illustrated in FIG. 1 by the significant degree of high frequency roll-off for the TOH curve 108 in FIG. 1 as compared to the dispersion model which has only a moderate high frequency roll-off. Curve 108 reflects a true diminished threshold of hearing capability which is noticeably more significant than would be expected based on the dispersion model alone.

It is important to recognize that the curve 108 in FIG. 1 is not the true frequency response of the hearing channel in FIG. 1. Instead, it is a TOH curve representing the measured ability to hear at the threshold of hearing level. This is an important distinction for reasons which shall be hereinafter explained in greater detail.

The importance of FIG. 1 is that it demonstrates that dispersion losses in the hearing channel cannot be accurately measured using conventional TOH techniques as are presently in use. In fact, it is now apparent that conventional TOH techniques for evaluating hearing loss are not measuring dispersion losses, but rather combined noise and dispersion effects (at least at higher frequencies where tinnitus noise is present). This is a significant problem because high fidelity hearing restoration requires accurate data as to the true nature of the dispersion losses. In particular, this information is essential for proper adjustment of hearing aids.

A conventional hearing aid will typically have several audio frequency bands and the gain of each band must be tailored for each individual person in order to counteract their particular loss of hearing (due to dispersion). However, it is apparent from the foregoing that conventional TOH measurements can give highly inaccurate results of dispersion losses due to the tinnitus problem described above. This improper data will translate to improper gain settings for the hearing aid, particularly at higher frequencies where the effects of tinnitus noise have distorted the measurement result. This conclusion is consistent with the complaints of many hearing aid users who claim that their hearing aids often sound tinny or give them only a very marginal improvement in intelligibility. It is clear that conventional approaches to hearing compensation distort sounds by incorrectly treating internal noise as thought it were dispersion.

Figure 2:
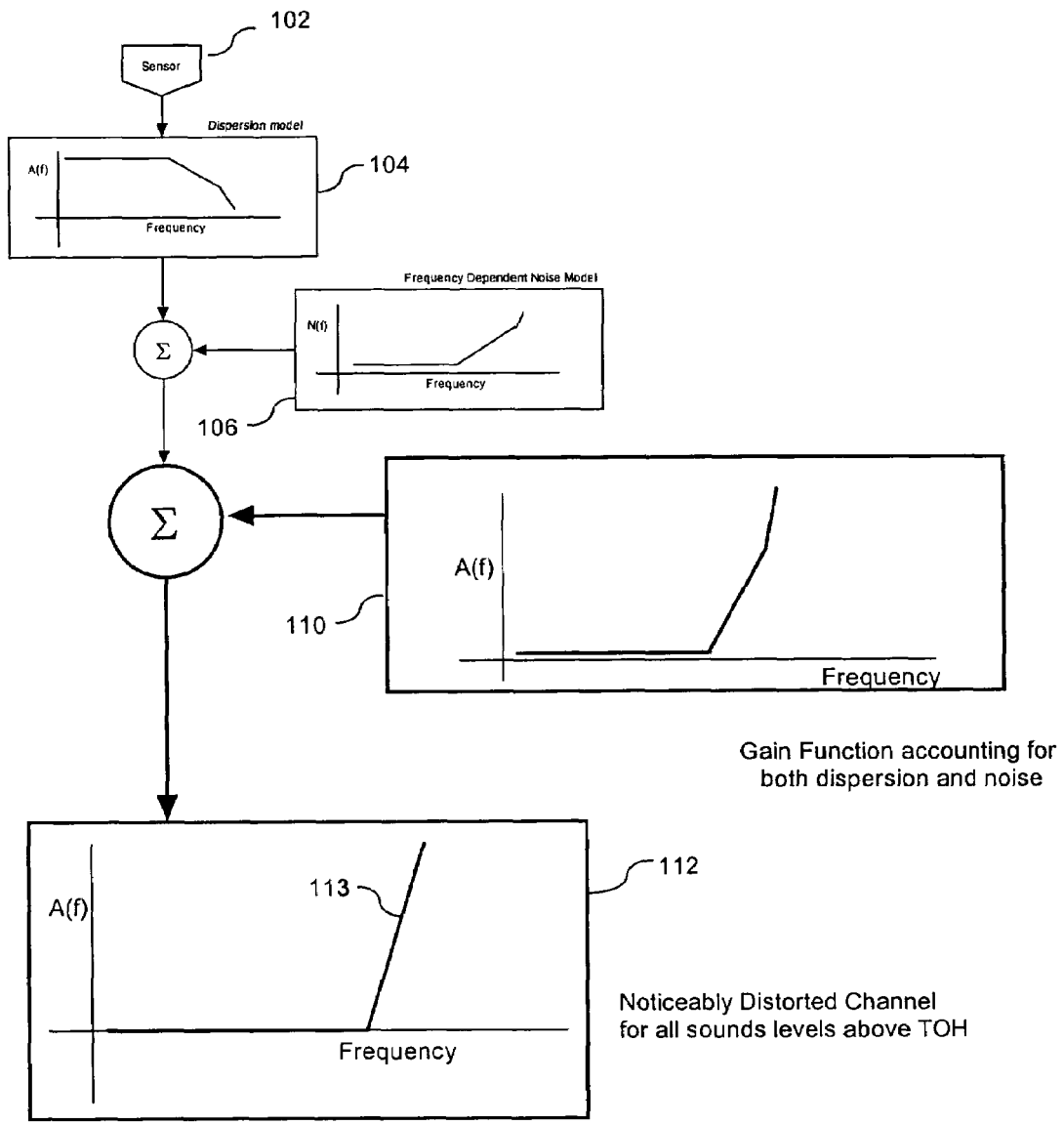
FIG. 2 is a block diagram illustrating the effects of conventional frequency dependent audio compensation schemes to correct measured hearing losses.

The foregoing distortion problem is illustrated in FIG. 2. The hearing channel model in FIG. 2 is modified relative to FIG. 1 so as to include a gain function 110 that is based on the threshold of hearing curve 108. However, instead of achieving a desirable flat (distortion free) frequency response, the net result will be an overall system response that is substantially distorted at the higher frequency range, reflecting excessive amounts of gain 113. This excessive gain at the higher frequencies creates distortion in the hearing channel and substantially inhibits intelligibility. In particular, sounds are unclear, unnaturally loud, sharp and tinny.

Figure 3:
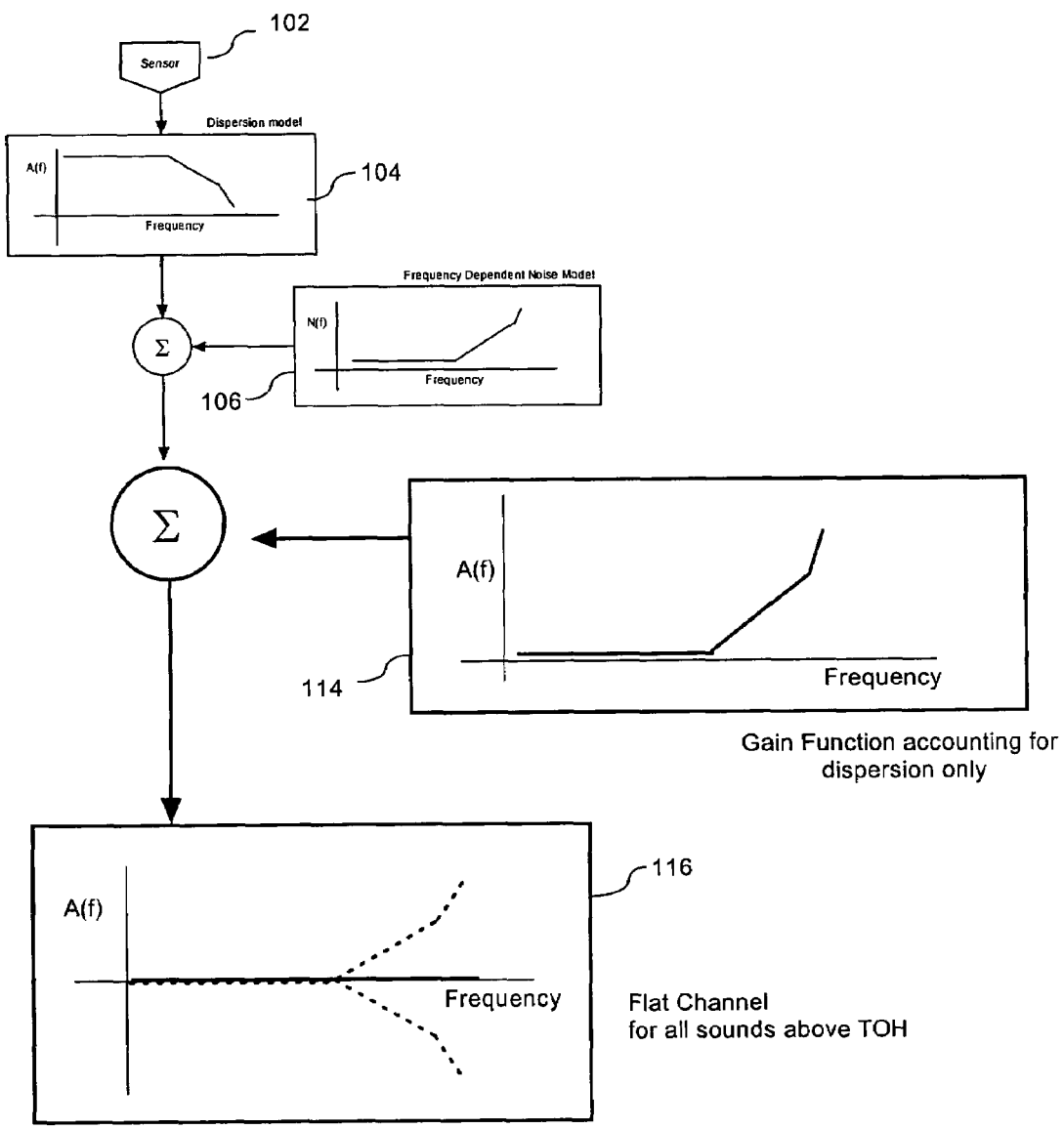
FIG. 3 is a block diagram that illustrates frequency dependent audio compensation in accordance with the inventive arrangements.

In contrast, the gain function 114 in FIG. 3 compensates only for the effects of dispersion model 104 (assuming that dispersion loss can be accurately measured by some means).

The net result is a channel that has a flat response (no distortion), and properly compensates for hearing losses due to dispersion. Weak high frequency sounds are still masked by tinnitus noise, but audio at conversation level and louder will be clearer. Based upon the foregoing, it is apparent that in order to avoid distortion in the channel, it is essential to have accurate data regarding dispersion losses.

In order to accurately measure dispersion losses, a measurement technique is required that makes the noise contribution negligible. One approach would be to apply Fletcher-Munson loudness contours at high acoustic input levels, well above TOH and above tinnitus noise. This approach can include selecting a series of audio tones within the normal range of hearing and measuring a relative sensitivity of a test subject with respect to the ability to hear each of the audio tones. One way this could be done is to determine for each tone an intensity necessary for a test subject to hear the tone at a standard equal loudness level. The standard loudness level can be selected to exceed a level of noise attributable to tinnitus for the test subject so that the noise has minimal contribution to the measurement. For example a minimum loudness level represented by curve 404 in FIG. 4 could be used as it is above the tinnitus level. All of the tone frequencies can be evaluated in this way to determine how much power is required for each one to achieve the same subjective loudness level for the test subject. This process is explained in greater detail in FIG. 5.

Figure 5:
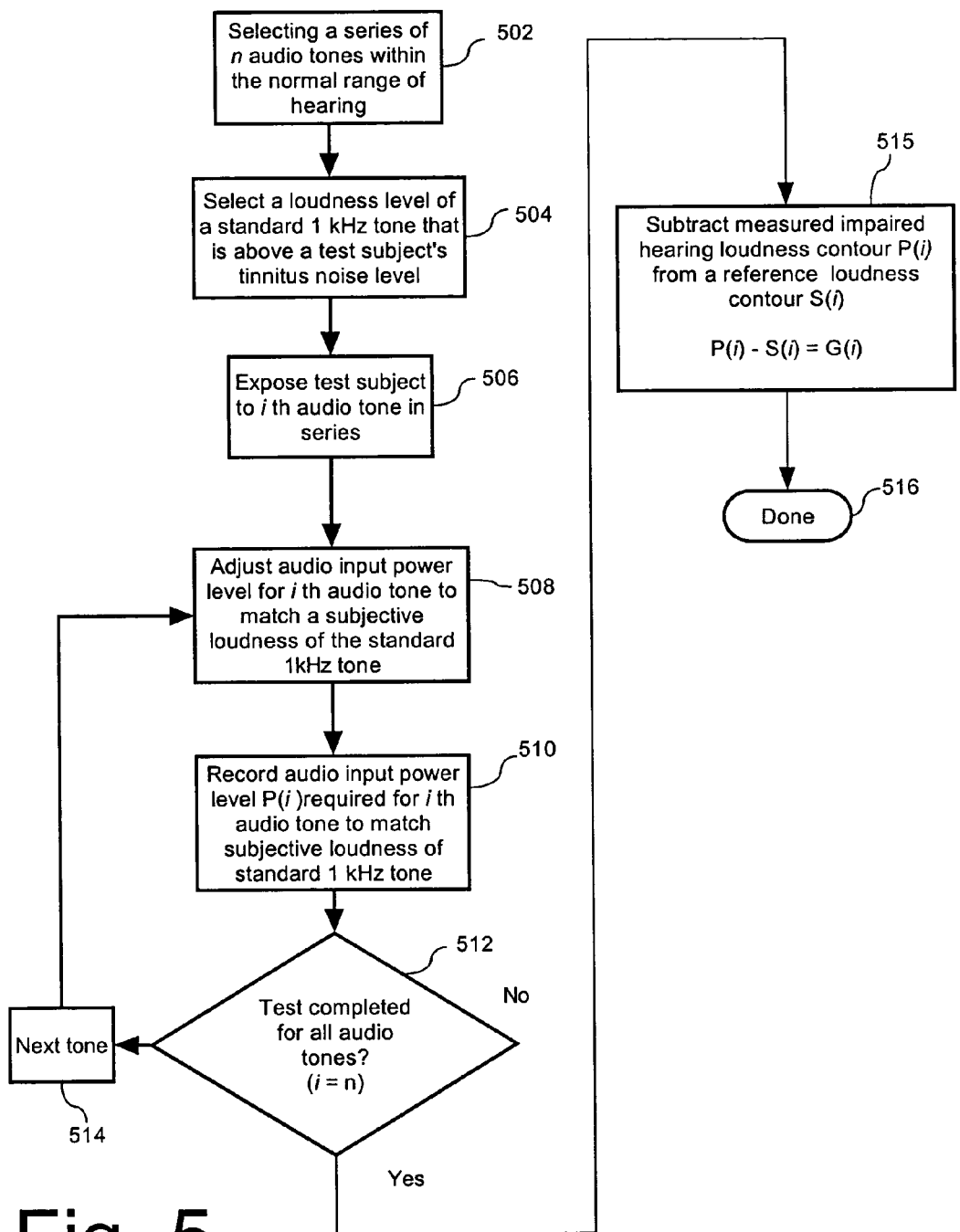
FIG. 5 is a flow chart illustrating one method for measuring dispersion losses in the hearing channel.

The process in FIG. 5 can begin in step 502 by selecting a series of n audio tones within the normal frequency range associated with human hearing. In step 504, a loudness level of a standard 1 kHz tone can be selected that is above a test subject's tinnitus noise level at all frequencies within the hearing range to be compensated. In step 506, the test subject can then be exposed to one of the tones in the series. For convenience, this shall be referred to as the ith tone.

In step 508, the audio input power level for the ith audio tone is adjusted to achieve a subjective loudness for the test subject that most closely matches the test subject's loudness evaluation of the standard 1 kHz tone. This can be accomplished by switching back and forth between the standard 1 kHz tone and the ith audio tone as the power level of the ith audio tone is adjusted. In step 510, the audio input power level necessary for achieving subjectively equal loudness is recorded. If the test is determined in step 510 to be complete for all n tones in the series, then the process can continue on to step 515. Otherwise, the next tone is selected in step 514 and the process continues at step 508 until all tones in the series have been evaluated.

In step 515, the required compensation gain curve can be determined. In particular, the required hearing compensation gain curve can be calculated by subtracting a reference (normal hearing) loudness curve (e.g. a Fletcher-Munson curve) from the subject's measured impaired hearing loudness contour (measured in steps 502 through 514. The reference loudness contour selected should correspond to the power level selected for the standard 1 kHz tone in step 504. More particularly, the reference loudness contour should be selected so that it approximately coincides with a 1 kHz tone of having a power level as selected in step 504.

Of course, those skilled in the art will appreciate that the invention is not limited to the particular test method described relative to FIG. 5. Instead, any process can be used, provided that it measures dispersion losses without substantial interference from the effects of tinnitus noise. For example, rather than relying upon subjective evaluations of loudness, it may be advantageous to rely on data from audio nerve impulses or EEG data to determine when a tone is being heard by the test subject at a standard loudness level. All such methods are intended as within the scope of the present invention, the method in FIG. 5 being merely one example.

It is also apparent that a family of responses at higher contours may be obtained in order to further improve the fidelity of hearing correction as a function of input acoustic level. However the approximate constancy of Fletcher-Munson loudness contours at and above conversational speech levels up to the threshold of pain suggest that determination of an individual's response at a single standard loudness level will be sufficient for most hearing compensation purposes.

Figure 6:
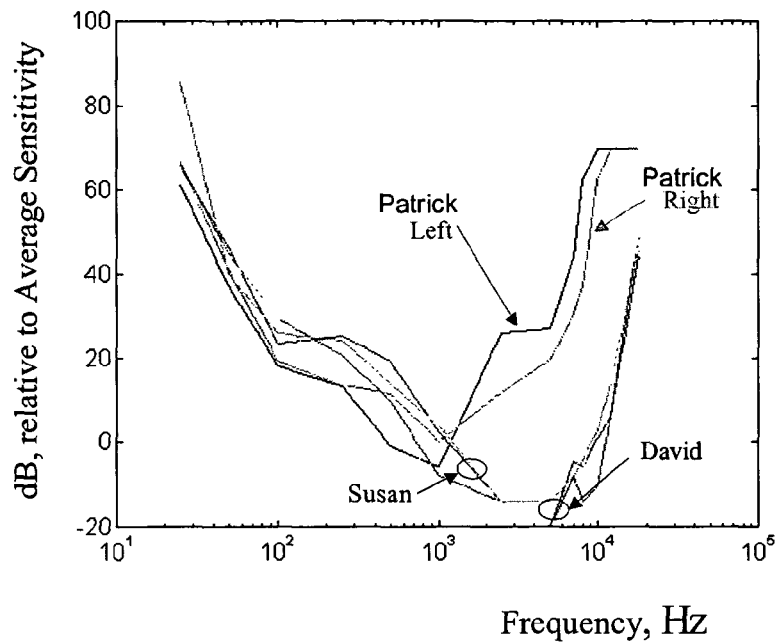
FIG. 6 is a data plot illustrating experimental results obtained using conventional threshold of hearing measurements.
Figure 7:
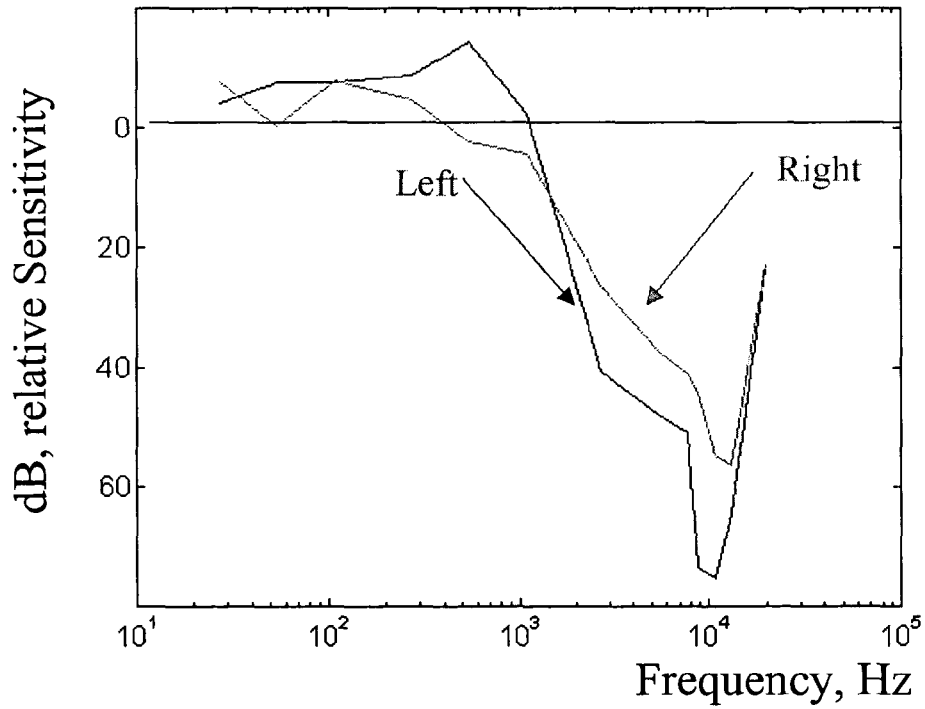
FIG. 7 is a curve showing apparent hearing loss relative to a standard threshold of hearing.
Figure 8:
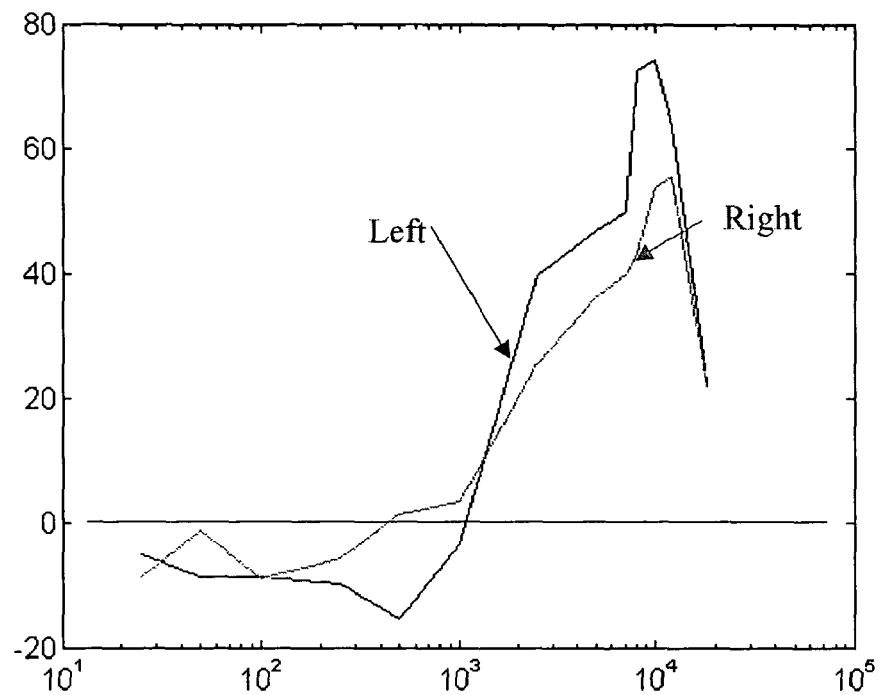
FIG. 8 is an erroneous gain function suggested by the data in FIGS. 6 and 7.

The dramatically different results achieved using the conventional TOH testing methods as compared to the test methods described herein with respect to FIG. 5 can be best understood by considering some actual test results which are illustrated in FIGS. 6-9. FIG. 6 shows the results of conventional TOH testing. The results for test subject Susan and David are normal. The test results for Patrick indicate substantially decreased sensitivity in the range above 1 kHz. The test results in FIG. 6 for Patrick can be used to calculate a new set of data which are illustrated in FIG. 7. The new set of data in FIG. 7 show measured hearing loss relative to standard TOH curve 400. The data for producing the curve in FIG. 7 is obtained by subtracting the measured hearing loss level from a standard TOH curve to obtain the apparent difference in gain. Inverting the curve in FIG. 7 produces the curve in FIG. 8. The inverted curve that is illustrated in FIG. 8 shows the apparent gain that would be required to compensate for the hearing loss suggested in FIG. 7. However, because the data in FIG. 5-7 does not exclude the effects of tinnitus noise, the suggested gain is incorrect and will produce distortion in the channel.

Figure 9:
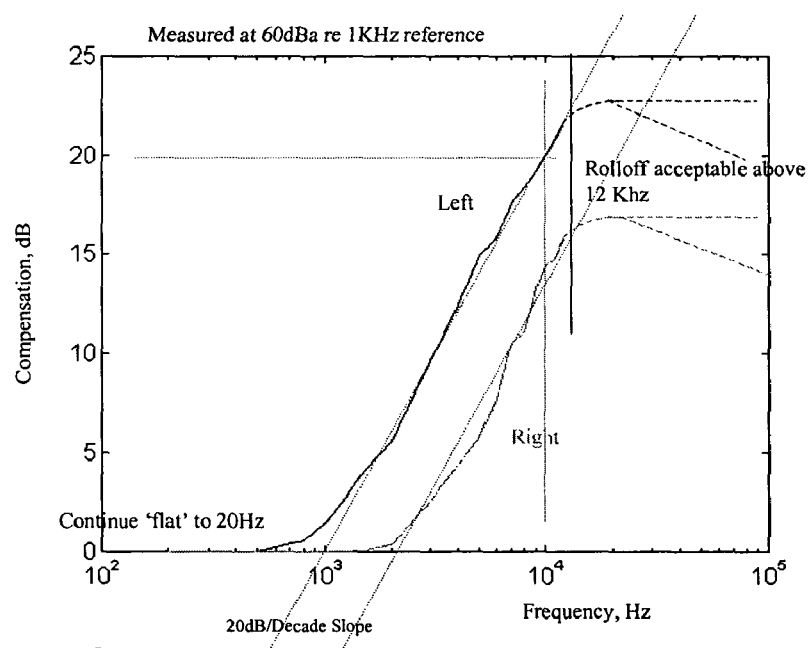
FIG. 9 is a correct gain function obtained using the inventive arrangements that should be used for the test subject represented in FIG. 8.

FIG. 9 shows the correct acoustic compensation which has been calculated using the process described in step 515 in FIG. 5. Referring to FIG. 9 it may be noted that, at least with regard to test subject Patrick, the required acoustic compensation is represented by a surprisingly simple 6 dB/octave (20 dB/Decade) slope. Further, the correct compensation, at least in this instance, involves about 40 dB to 50 dB less peak high frequency gain as compared to the amount suggested by erroneous conventional TOH testing. The difference in results explains why so many hearing aid users are dissatisfied with the results obtained using conventional hearing aid techniques.

Another interesting difference that may be noted when comparing the gain functions specified by FIGS. 8 and 9 is that the gain specified in FIG. 9 as a result of using the inventive techniques herein specifies continued increases in gain above 10 kHz, whereas the erroneous TOH technique rolls off sharply at 10 kHz. The additional gain above 10 kHz is not a range that is commonly addressed by audiologists and suppliers. However, it is important for speech consonants and fricatives, as well as musical subtleties.

Tests in which the acoustic compensation is set in accordance with the inventive arrangements have shown dramatically improved results as compared to conventional compensation methods. Qualitatively, it was found that song lyrics were clear and understandable (if sung clearly), consonants and fricatives were clearly perceived. Subtle percussion sounds such as bells and chimes were also clearly perceived. Most importantly, the ability to understand words and sentences (including whispered words) was dramatically improved.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

I claim:

1. A method for accurately measuring hearing loss, comprising the steps of:
    selecting a series of audio tones within the normal range of hearing;
    measuring a relative sensitivity of a test subject with respect to the ability to hear each of said audio tones, exclusive of the effects of tinnitus, said measuring step including selecting a plurality of audio tones, and determining for each said audio tone an intensity necessary for a test subject to hear said audio tone at a subjectively equal loudness level; and
    determining a difference between said intensity measured for each of said audio tones and an intensity predicted by a standard loudness contour for each of said audio tones;
    wherein said subjectively equal loudness level exceeds a noise level attributable to said tinnitus at a frequency of each said audio tone.

2. A method for accurately measuring hearing loss, comprising the steps of:
    selecting a series of audio tones within the normal range of hearing;
    measuring a relative sensitivity of a test subject with respect to the ability to hear each of said audio tones, exclusive of the effects of tinnitus said measuring step including determining for each said audio tone an intensity necessary for said test subject to hear said audio tones at a subjectively equal loudness level which exceeds a noise level attributable to said tinnitus at a frequency of each said audio tone; and
    determining a difference between said intensity measured for each of said audio tones and an intensity predicted by a standard loudness contour for each of said audio tones.

3. The method according to claim 2 further comprising the step of selecting said standard loudness contour to be at least one of a Fletcher-Munson Loudness Contour and a functional equivalent of a Fletcher-Munson Loudness Contour.

4. The method according to claim 1 further comprising the step of measuring a noise level attributable to tinnitus.

5. The method according to claim 1 further comprising the step of configuring at least one gain setting of a hearing aid to compensate for said hearing loss determined in said measuring step.

6. A method for setting a frequency dependent audio gain of a hearing aid device for a person suffering from tinnitus, comprising the steps of:
    measuring a test subject's loss of hearing attributable exclusively to dispersion in the hearing channel; and
    setting for each of a plurality of frequency bands of said hearing aid device an audio gain level to compensate exclusively for said dispersion loss;
    wherein said measuring step comprises selecting a plurality of audio tones, determining for each said audio tone an intensity necessary for a test subject to hear said audio tone at a subjectively equal loudness level which exceeds a noise level attributable to tinnitus at a frequency of each said audio tone, and determining a difference between said intensity measured for each of said audio tones and an intensity predicted by a standard loudness contour for each of said audio tones.

7. A method for setting a frequency dependent audio gain of a hearing aid device for a person suffering from tinnitus, comprising the steps of:
    measuring a test subject's loss of hearing attributable exclusively to dispersion in the hearing channel, wherein said measuring a test subject's loss of hearing comprises selecting a series of audio tones within the normal range of hearing and measuring a relative sensitivity of said test subject with respect to the ability to hear each of said audio tones, exclusive of the effects tinnitus noise;
    setting for each of a plurality of frequency bands of said hearing aid device an audio gain level to compensate exclusively for said dispersion loss;
    determining for each audio tone an intensity necessary for said test subject to hear said audio tone at a subjectively equal loudness level which exceeds a noise level attributable to said tinnitus at a frequency of each said audio tone; and
    determining a difference between said intensity measured for each of said audio tones and a predicted intensity indicated by a standard loudness contour for each of said audio tones.

8. The method according to claim 7 further comprising the step of selecting said standard loudness contour to be a Fletcher-Munson Loudness Contour.

9. A method for providing high fidelity hearing restoration, comprising the steps of:
    measuring a test subject's loss of hearing attributable exclusively to dispersion in the hearing channel;
    setting for each of a plurality of frequency bands of a hearing aid device an audio gain level to compensate exclusively for said dispersion; and
    wherein said measuring step comprises selecting a plurality of audio tones, determining for each said audio tone an intensity necessary for a test subject to hear said audio tone at a subjectively equal loudness level which exceeds a noise level attributable to tinnitus at a frequency of each said audio tone, and determining a difference between said intensity measured for each of said audio tones and an intensity predicted by a standard loudness contour for each of said audio tones.

10. A method for accurately measuring hearing loss, comprising the steps of:
    selecting a series of audio frequencies within the normal range of hearing; and
    measuring a test subject's loss of hearing at each frequency attributable exclusively to dispersion in the hearing channel;
    wherein said measuring step comprises selecting a plurality of audio tones, determining for each said audio tone an intensity necessary for a test subject to hear said audio tone at a subjectively equal loudness level which exceeds a noise level attributable to tinnitus at a frequency of each said audio tone, and determining a difference between said intensity measured for each of said audio tones and an intensity predicted by a standard loudness contour for each of said audio tones.

* * * * *